United States Patent
Kim

(10) Patent No.: US 11,759,489 B2
(45) Date of Patent: Sep. 19, 2023

(54) **FOOD COMPOSITION FOR PROMOTING HEIGHT GROWTH AND PHARMACEUTICAL COMPOSITION FOR PROMOTING HEIGHT GROWTH INCLUDING *HUMULUS JAPONICUS* EXTRACT OR GROUND *HUMULUS JAPONICUS* AS ACTIVE INGREDIENT**

(71) Applicants: PENS CO., LTD., Seoul (KR); Hong Sik Kim, Goyang-si (KR)

(72) Inventor: Hong Sik Kim, Goyang-si (KR)

(73) Assignees: PENS CO., LTD., Seoul (KR); Hong Sik KIM, Goyang-si (KR)

( * ) Notice: Subject to any disclaimer, the term of this patent is extended or adjusted under 35 U.S.C. 154(b) by 188 days.

(21) Appl. No.: 17/252,575

(22) PCT Filed: Aug. 22, 2019

(86) PCT No.: PCT/KR2019/010687
§ 371 (c)(1),
(2) Date: Dec. 15, 2020

(87) PCT Pub. No.: WO2020/222366
PCT Pub. Date: Nov. 5, 2020

(65) Prior Publication Data
US 2021/0252089 A1 Aug. 19, 2021

(30) Foreign Application Priority Data
Apr. 30, 2019 (KR) .................. 10-2019-0050164

(51) Int. Cl.
*A61K 36/185* (2006.01)
*A23L 33/105* (2016.01)
*A23L 33/00* (2016.01)
*A61K 9/00* (2006.01)
*A61K 36/42* (2006.01)
*A61K 36/8962* (2006.01)

(52) U.S. Cl.
CPC .......... *A61K 36/185* (2013.01); *A23L 33/105* (2016.08); *A23L 33/40* (2016.08); *A61K 9/0056* (2013.01); *A61K 36/42* (2013.01); *A61K 36/8962* (2013.01); *A23V 2002/00* (2013.01)

(58) Field of Classification Search
None
See application file for complete search history.

(56) References Cited

U.S. PATENT DOCUMENTS 6,900,281 B2 * 5/2005 Streeky .................. C08F 10/00
526/348
2014/0377383 A1 12/2014 Sun et al.
2018/0078525 A1 3/2018 Kim et al.

FOREIGN PATENT DOCUMENTS

| CN | 101548708 A | 10/2009 | |
|---|---|---|---|
| CN | 101642193 A | 2/2010 | |
| CN | 103432364 A | 12/2013 | |
| CN | 103609900 A | 3/2014 | |
| CN | 103919932 A | 7/2014 | |
| CN | 104256690 A | 1/2015 | |
| CN | 106615634 A | 5/2017 | |
| CN | 107410728 A | 12/2017 | |
| CN | 108114207 A | 6/2018 | |
| CN | 109418563 A | 3/2019 | |
| KR | 10-2004-0092861 A | 11/2004 | |
| KR | 10-2008-0109359 A | 12/2008 | |
| KR | 10-2011-0055940 A | 5/2011 | |
| KR | 10-1043509 B1 | 6/2011 | |
| KR | 10-1067028 B1 | 9/2011 | |
| KR | 10-2013-0102295 A | 9/2013 | |
| KR | 10-2014-0019707 A | 2/2014 | |
| KR | 10-2014-0057709 A | 5/2014 | |
| KR | 10-2016-0025073 A | 3/2016 | |
| KR | 10-2017-0000902 A | 1/2017 | |
| WO | 2015/009047 A1 | 1/2015 | |
| WO | WO-2016006947 A1 * | 1/2016 | ........... A23L 33/105 |

OTHER PUBLICATIONS

Lee et al. (2012) Korean J. Food and Nutr. vol. 25, No. 2, pp. 357-361. (Year: 2012).*
Raskin et al. (2004) Current Pharmaceutical Design 10, 3419-3429. (Year: 2004).*
Revilla et al. (1998) J. Agric. Food Chem. 46, 4592-4597. (Year: 1998).*
Seung-Woo Park, et al., "Antimutagenic Effects and Isolation of Flavonoids from Humulus japonicus Extract", Korean J. Food Sci. Technol, 1995, pp. 897-901, vol. 27, No. 6.
Tae-Ho Kim, et al., "The effects of luteolin on osteoclast differentiation, function in vitro and ovariectomy-induced bone loss", Journal of Nutritional Biochemistry, 2011, pp. 8-15, vol. 22.
Christophe Prouillet, et al., "Stimulatory effect of naturally occurring flavonols quercetin and kaempferol on alkaline phosphatase activity in MG-63 human osteoblasts through ERK and estrogen receptor pathway", Biochemical Pharmacology, 2004, pp. 1307-1313, vol. 67.
M. Mukherjee, et al., "Prevention of Bone Loss by Oil Extract of Garlic (*Allium sativum* Linn.) in an Ovariectomized Rat Model of Osteoporosis", Phytotherapy Research, 2004, pp. 389-394, vol. 18.
Maryam Mahmood, "The Effects of Freeze-Dried Watermelon On Bone and Clinical Parameters of Ovariectomized Mice", Thesis of the degree of master of science, Benedictine University, 2011, 73 pages.
International Search Report for PCT/KR2019/010687 dated Jan. 29, 2020 (PCT/ISA/210).
Extended European Search Report issued in EP application No. 19927281.6, dated Nov. 21, 2022.

* cited by examiner

*Primary Examiner* — Russell G Fiebig
(74) *Attorney, Agent, or Firm* — Sughrue Mion, PLLC

(57) ABSTRACT

The present invention provides a health functional food composition for promoting height growth comprising a *Humulus japonicus* extract or a *Humulus japonicus* crushed product as an active ingredient and a composition for promoting height growth comprising a watermelon/garlic concentrate in addition to a *Humulus japonicus* extract or a *Humulus japonicus* crushed product.

4 Claims, 4 Drawing Sheets

[Figure 1]
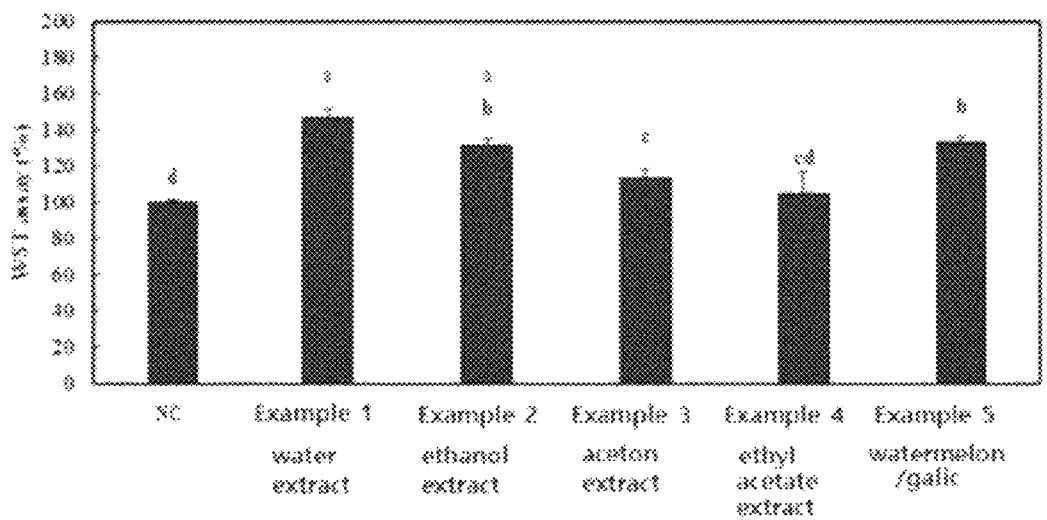
The results were presented means±SD. Different letters show a significantly difference at P<0.05 as determined by Duncan's multiple range test.
[Figure 2]
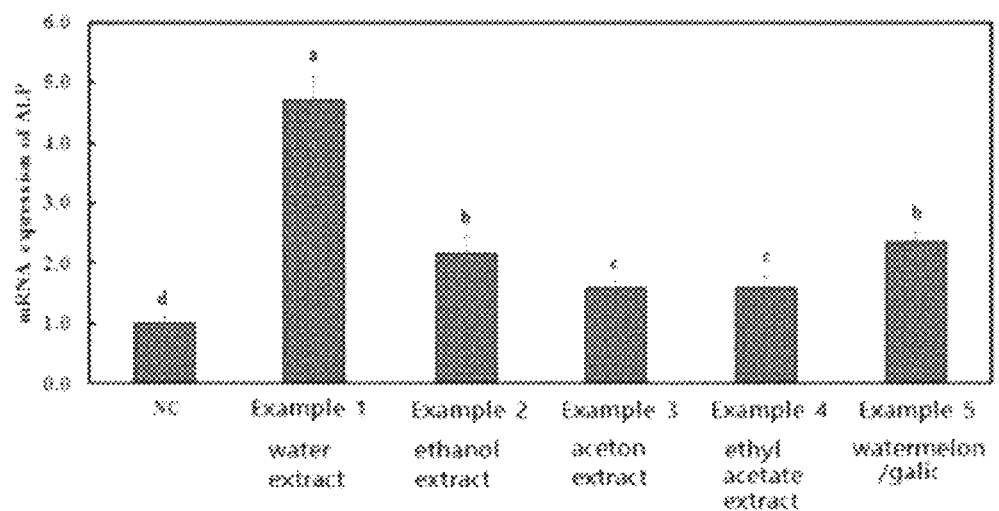
The results were presented means±SD. Different letters show a significantly difference at P<0.05 as determined by Duncan's multiple range test.

[Figure 3]
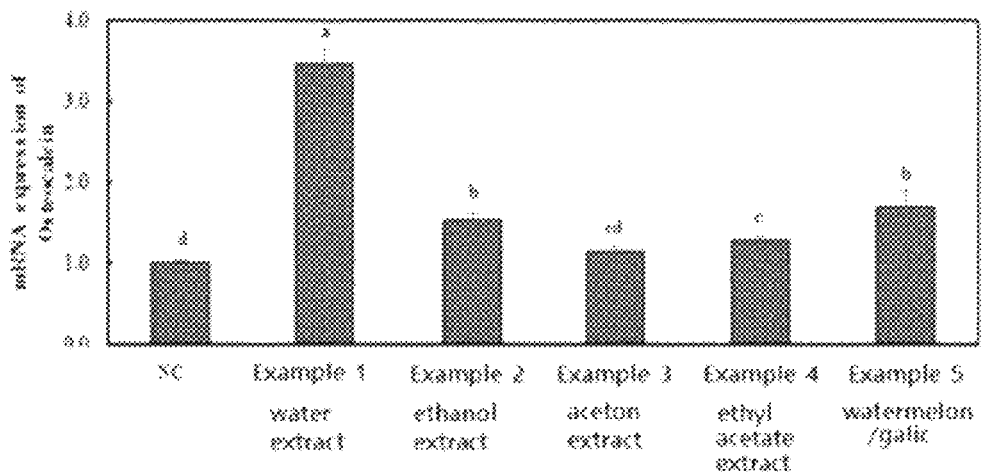
The results were presented means±SD. Different letters show a significantly difference at P<0.05 as determined by Duncan's multiple range test.
[Figure 4]
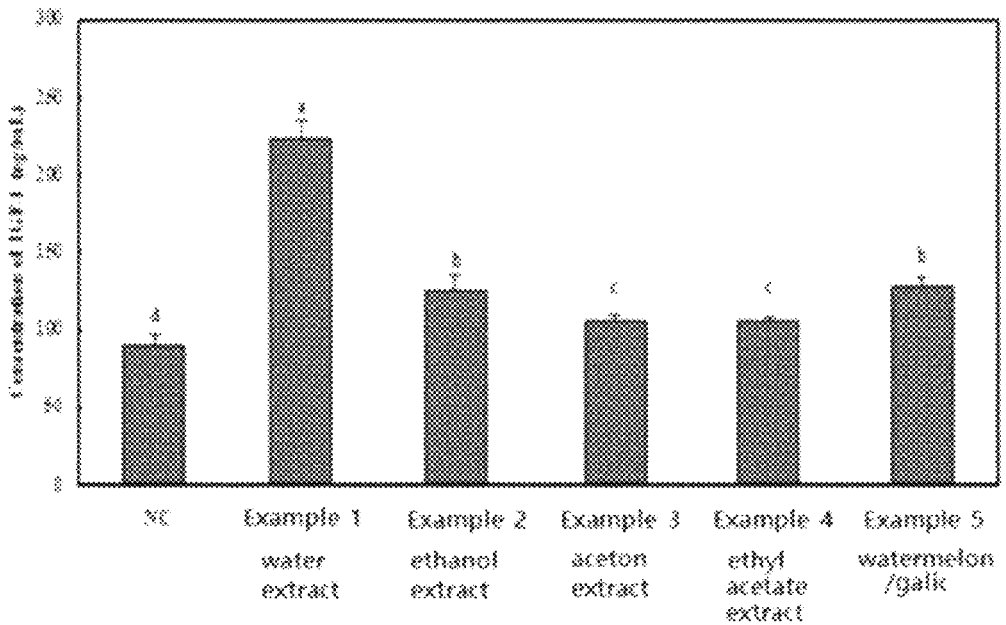
The results were presented means±SD. Different letters show a significantly difference at P<0.05 as determined by Duncan's multiple range test.

[Figure 5]
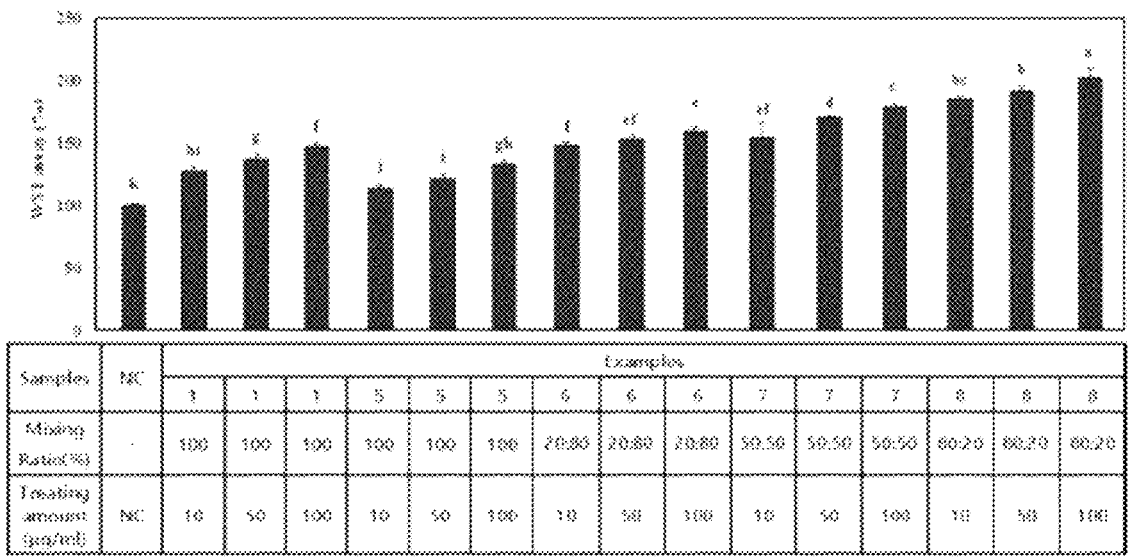
[Figure 6]
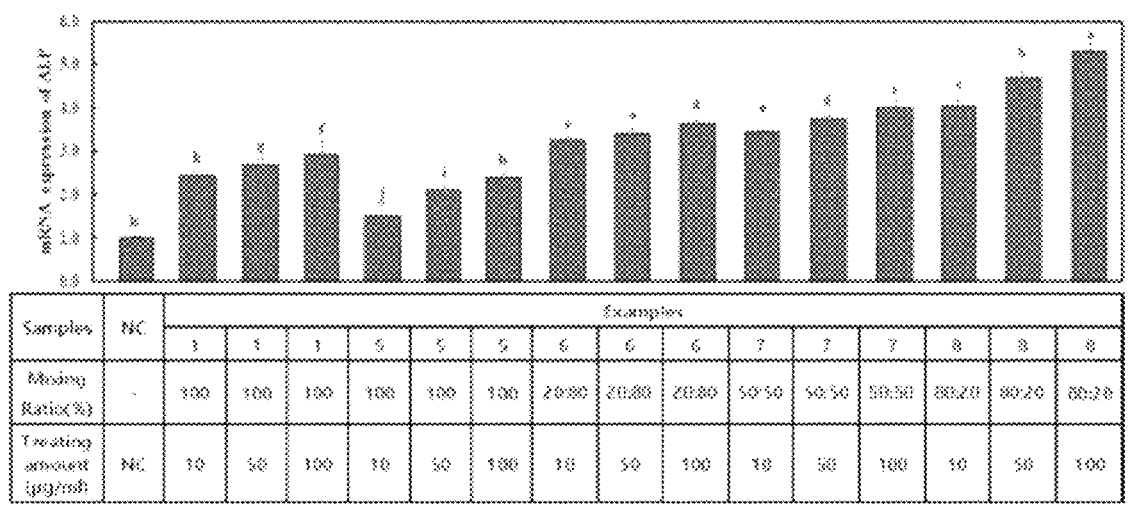

[Figure 7]
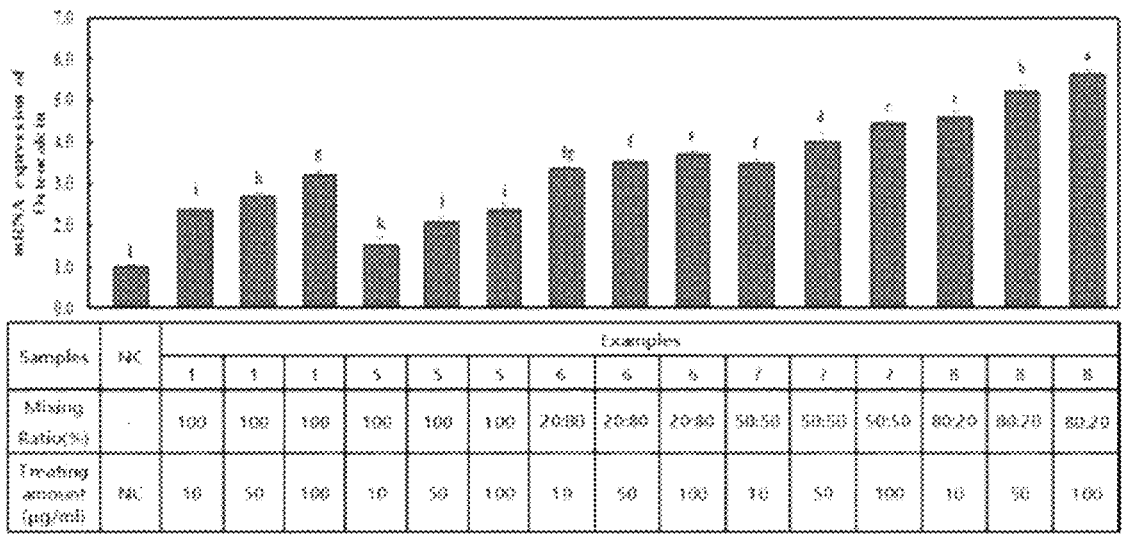
[Figure 8]
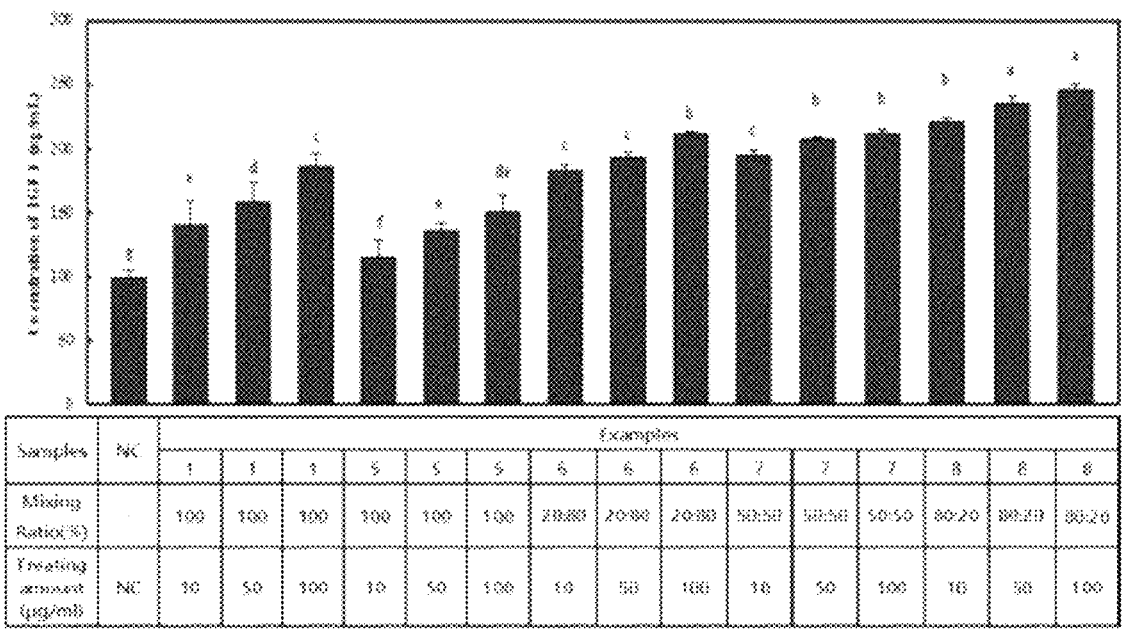

FOOD COMPOSITION FOR PROMOTING HEIGHT GROWTH AND PHARMACEUTICAL COMPOSITION FOR PROMOTING HEIGHT GROWTH INCLUDING *HUMULUS JAPONICUS* EXTRACT OR GROUND *HUMULUS JAPONICUS* AS ACTIVE INGREDIENT

CROSS REFERENCE TO RELATED APPLICATIONS

This application is a National Stage of International Application No. PCT/KR2019/010687 filed Aug. 22, 2019, claiming priority based on Korean Patent Application No. 10-2019-0050164 filed Apr. 30, 2019.

TECHNICAL FIELD

The present invention relates to a food composition and a pharmaceutical composition for promoting height growth comprising a *Humulus japonicus* ingredient as an active ingredient.

BACKGROUND ART

In our society, due to recent economic growth, the growth conditions of infants, children, and adolescents have been greatly improved by improvement in nutritional status and changes in dietary habits. In general, the meaning of growth is often limited to an increase in height, but medically, the morphological and anatomical sizes and functions are increased, and the growth involves that the skeleton and muscles are enlarged and strengthened, and such growth is achieved by the action of hormones.

As methods for promoting the growth, methods such as administration of growth hormone preparations, Ilizarov surgery, and the like have been known, but these methods are very concerned about the accompanying side effects, and methods such as administration of health functional foods have disadvantages of not providing sufficient effects.

In other words, the administration of growth hormones may cause various side effects, such as leukemia, hypothyroidism, hyperglycemia, central nervous system tumors, diabetes and epilepsy, etc. In addition, the Ilizarov surgery is a surgical method that is mainly used when the lengths of both lower limbs are asymmetric, but when the surgery is performed on a normal and short person, serious side effects may occur to prevent normal walking.

In recent studies, a method of using natural substances is attracting attention as a method of safely inducing the growth while avoiding side effects from administration of growth hormones and side effects from surgery. Specifically, a method for ultimately inducing height growth by stimulating the secretion of growth hormones by naturally ingesting natural substances has been found, and accordingly, the search for the natural substances is being actively conducted.

However, despite the active research activities as described above, natural substances capable of providing a substantial effect on height growth have been not yet reported.

PRIOR ART DOCUMENT

Korean Laid-open Patent Publication No. 10-2014-0057709

DISCLOSURE

Technical Problem

The present inventors have made many efforts to solve the above problems, found a plant having an excellent activity in promoting height growth as a medicinal plant that has been used for various symptoms in the related art and a method capable of enhancing its activity, and then completed the present invention.

Therefore, an object of the present invention is to provide a composition for promoting height growth capable of efficiently promoting the height growth without side effects by using a natural substance.

Technical Solution

In order to achieve the object, the present invention provides a composition for promoting height growth comprising a *Humulus japonicus* ingredient as an active ingredient.

In an embodiment of the present invention, the composition for promoting the height growth may further comprise at least one selected from the group consisting of watermelon and garlic.

In an embodiment of the present invention, at least one selected from the group consisting of watermelon and garlic may be a watermelon/garlic concentrate processed in the form of concentrate prepared by mixing watermelon and garlic in a weight ratio of 1:9 to 9:1.

In an embodiment of the present invention, the composition for promoting the height growth may be used as a pharmaceutical composition or food composition.

Advantageous Effects

According to the present invention, the composition for promoting the height growth comprises a *Humulus japonicus* ingredient having a very excellent activity for promoting the height growth or a watermelon and/or garlic ingredient enhancing a height growth promoting effect by providing synergy with the *Humulus japonicus* ingredient in addition to the *Humulus japonicus* ingredient to provide a very excellent effect on the height growth of children and adolescents in a growth period.

DESCRIPTION OF DRAWINGS

FIG. 1 is a graph showing measuring effects of *Humulus japonicus* extracts in Examples 1 to 4 of the present invention and a watermelon/garlic concentrate sample in Example 5 on proliferation of MG63 cells.

FIG. 2 is a graph showing measuring effects of *Humulus japonicus* extracts in Examples 1 to 4 of the present invention and a watermelon/garlic concentrate sample in Example 5 on ALP gene expression of MG63 cells.

FIG. 3 is a graph showing measuring effects of *Humulus japonicus* extracts in Examples 1 to 4 of the present invention and a watermelon/garlic concentrate sample in Example 5 on osteocalcin gene expression of MG63 cells.

FIG. 4 is a graph showing measuring effects of *Humulus japonicus* extracts in Examples 1 to 4 of the present invention and a watermelon/garlic concentrate sample in Example 5 on a concentration of IGF-1 protein.

FIG. 5 is a graph showing measuring effects of composition samples containing a *Humulus japonicus* extract and a watermelon/garlic concentrate in Examples 6 to 8 of the present invention prepared by varying a mixing ratio, respectively, on proliferation of MG63 cells.

FIG. 6 is a graph showing measuring effects of composition samples containing a *Humulus japonicus* extract and a watermelon/garlic concentrate in Examples 6 to 8 of the present invention prepared by varying a mixing ratio, respectively, on ALP gene expression of MG63 cells.

FIG. 7 is a graph showing measuring effects of composition samples containing a *Humulus japonicus* extract and a watermelon/garlic concentrate in Examples 6 to 8 of the present invention prepared by varying a mixing ratio, respectively, on osteocalcin gene expression of MG63 cells.

FIG. 8 is a graph showing measuring effects of composition samples containing a *Humulus japonicus* extract and a watermelon/garlic concentrate in Examples 6 to 8 of the present invention prepared by varying a mixing ratio, respectively, on a concentration of IGF-1 protein.

BEST MODE OF THE INVENTION

Terms used in the present invention are terms defined in consideration of functions in the present invention, and may vary according to the intentions of users and operators or customs, and thus, definitions of these terms should be made based on the technical contents throughout the present specification. On the other hand, embodiments are only exemplary matters of components presented in the appended claims of the present invention, and do not limit the scope of the present invention, and the scope of the present invention should be interpreted based on the technical idea throughout the specification of the present invention.

Hereinafter, the present invention will be described in more detail.

The present invention relates to a composition for promoting height growth comprising a *Humulus japonicus* ingredient as an active ingredient.

The *Humulus japonicus* ingredient may be at least one selected from the group consisting of a processed product containing a *Humulus japonicus* substrate and a *Humulus japonicus* extract, but is not limited thereto. For example, it should be understood that *Humulus japonicus* processed in the form of use of a medicinal plant known in the art is all included in the *Humulus japonicus* ingredient.

The processed product containing the *Humulus japonicus* substrate includes, for example, a processed product obtained by drying or steaming *Humulus japonicus*, and a processed product (crushed product) in a pulverized or crushed form. However, the processed product is not limited thereto, and it should be understood that all processed forms containing the *Humulus japonicus* substrate are included in the processed product containing the *Humulus japonicus* substrate of the present invention.

The *Humulus japonicus* extract may be, for example, an extract extracted with at least one solvent selected from the group consisting of water, alcohol, acetone, and ethyl acetate. In particular, among these extracts, extracts extracted with hot water may be preferably used.

Ethyl alcohol (ethanol) may be preferably used as the alcohol.

The *Humulus japonicus* used in the present invention is also called Yulcho, Galryulman, and Galryukman, and has been known as *Humulus japonica* Sidb. et Zucc. or *H. scandens* Merr. The *Humulus japonicus* grows by the brook and the road and at the foot of a mountain in various places, and is usually used by cutting the turning leafy in summer and drying the cut turning in the shade.

The *Humulus japonicus* is known to have a sweet and bitter taste and a cold nature, and to lower heat, detoxify, eliminate bloodstasis, and give urine well. Through pharmacological experiments, coercive action, diuretic action, and inhibitory action against Gram-positive bacteria have also been found.

Also, it is known to be effective when a patient has a fever, feels stuffy, and thirsty; when a patient has a fever due to malaria and tuberculosis; and in digestive disorders, acute gastritis, edema, diarrhea, dysentery, cystitis, urethritis, pregnancy, urethral stones, hypertension, boils, and the like.

However, until now, it has not been known at all that the *Humulus japonicus* has a height growth promoting activity. This fact has been confirmed through clinical trials while the inventors of the present invention operate an oriental medicine clinic, and has been more scientifically proven through experiments and the like conducted for the filling of the present invention.

The *Humulus japonicus* may use at least one selected from leaves, sprouts, stems, and roots, and the *Humulus japonicus* extract is more preferably extracted from, particularly, leaves and sprouts.

The composition for promoting the height growth of the present invention may further comprise at least one selected from the group consisting of watermelon and garlic in addition to the *Humulus japonicus* ingredient.

At least one selected from the group consisting of watermelon and garlic causes a synergistic effect with the *Humulus japonicus* ingredient, and thus, performs a function of enhancing the activity of the *Humulus japonicus* ingredient.

At least one selected from the group consisting of watermelon and garlic may be preferably used to be processed in a concentrate form. The preparation of the concentrate may be performed by methods known in the art.

In particular, the watermelon/garlic concentrate, which is processed in the concentrate form by mixing watermelon and garlic in a weight ratio of 1:9 to 9:1, exhibits an excellent synergistic effect with the *Humulus japonicus* ingredient. Therefore, it is preferred to use this concentrate form together with the *Humulus japonicus* ingredient. The mixing weight ratio of the watermelon and garlic is more preferably 2:8 to 5:5.

The watermelon/garlic concentrate may be prepared by a method for producing a concentrate known in the art. Particularly, the watermelon/garlic concentrate may be preferably prepared by a process of heating while applying a pressure of 1 to 1.5 kg in a pressed cooker.

The heating may be performed at a temperature of 50° C. to 200° C., more preferably 100° C. to 180° C., and much more preferably 150° C. to 170° C. The heating may be performed at a time of 1 to hours, more preferably 10 to 20 hours, and much more preferably 14 to 18 hours.

In the present invention, the *Humulus japonicus* ingredient and at least one selected from the group consisting of watermelon and garlic may be included in a weight ratio of 1:9 to 9:1, preferably 2:8 to 9:1, more preferably 5:5 to 9:1, much more preferably 7:3 to 9:1.

When the *Humulus japonicus* ingredient and at least one selected from the group consisting of watermelon and garlic are included in the aforementioned range, it is preferable because the height growth promoting activity may be maximized by the synergistic effect of the respective ingredients.

The composition for promoting the height growth of the present invention may be used as a pharmaceutical composition or a food composition.

When the composition for promoting the height growth of the present invention is used as the pharmaceutical composition, the composition may further comprise at least one additive selected from the group consisting of a pharmaceutically acceptable carrier, an excipient, and a diluent. As described above, the types and amounts of additives additionally included in the pharmaceutical composition of the present invention are followed as commonly known in the related art.

The pharmaceutical composition may comprise a pharmaceutically acceptable carrier. The composition comprising the pharmaceutically acceptable carrier may be formulated into various oral or parenteral formulations.

For the formulation, a diluent or an excipient may be used, such as a filler, an extender, a binder, a wetting agent, a disintegrating agent, a surfactant, and the like, which are generally used.

As the pharmaceutical composition, a solid formulation for oral administration includes a tablet, a pill, a powder, a granule, a capsule, and the like, and the solid formulation may be prepared by mixing at least one excipient, for example, starch, calcium carbonate, sucrose or lactose, gelatin, and the like with at least one compound. Further, lubricants such as magnesium stearate, talc, and the like may be used in addition to simple excipients.

A liquid formulation for oral administration may correspond to a suspension, an oral liquid, an emulsion, a syrup, and the like, and may include various excipients, for example, a wetting agent, a sweetener, an aromatic agent, a preserving agent, and the like, in addition to water and liquid paraffin which are commonly used as simple diluents.

A formulation for parenteral administration includes a sterile aqueous solution, a non-aqueous solution, a suspension, an emulsion, a lyophilizing agent, and a suppository.

As the non-aqueous solution and the suspension, propylene glycol, polyethylene glycol, vegetable oil such as olive oil, injectable ester such as ethyl oleate, and the like may be used.

As a base of the suppository, witepsol, macrogol, tween 61, cacao butter, laurinum, glycerogelatin, and the like may be used.

The pharmaceutical composition may be formulated and used to be suitable for an application form in the form of oral formulations such as tablets, pills, powders, granules, capsules, suspensions, oral liquids, emulsions, and syrups; and parenteral formulations such as aqueous solutions as sterilized injection solutions, non-aqueous solvents, suspensions, and emulsions, lyophilized preparations, suppositories, etc.

The route of administration of the pharmaceutical composition may be administered through any general route as long as the pharmaceutical composition can reach a target tissue. For example, according to a purpose, the pharmaceutical composition may be injected by intraperitoneal administration, intravenous administration, arterial administration, intramuscular administration, intraosseous administration, intrauterine administration, dural administration, subcutaneous administration, intradermal administration, oral administration, intranasal administration, intrapulmonary administration, rectal administration, and intracerebroventricular administration, but is not limited thereto. In addition, the pharmaceutical composition may be administered by any device capable of transferring an active ingredient to a target cell.

The pharmaceutical composition may be administered in a pharmaceutically effective dose. In the present invention, the term "pharmaceutically effective dose" refers to a amount enough to treat diseases at a reasonable benefit/risk ratio applicable to medical treatment, and an effective dose level may be determined according to elements including a kind of subject, the severity, age, gender, a type of infected virus, the activity of a drug, sensitivity to a drug, a time of administration, a route of administration, an excretion rate, duration of treatment, and drugs to be simultaneously used, and other elements well-known in the medical field.

The pharmaceutical composition may be administered as an individual therapeutic agent or administered in combination with other therapeutic agents, and sequentially or simultaneously administered with therapeutic agents in the related art. In addition, the pharmaceutical composition may be administered singly or multiple. It is important to administer an amount capable of obtaining a maximum effect with a minimal amount without side effects in consideration with all the elements, and the amount thereof may be easily determined by those skilled in the art.

The pharmaceutical composition may be used alone or in combination with surgery, hormone therapy, drug therapy, and methods using biological response modifiers for therapy for promoting height growth. The pharmaceutical composition may be used for preventing or treating dwarfism or nanism.

In addition, the composition of the present invention may be a food composition for promoting height growth.

The food composition may comprise an additional ingredient capable of commonly enhancing odor, taste, vision, and the like. For example, vitamins A, D, E, B1, B2, B6, B12, niacin, biotin, folate, panthotenic acid, and the like may be included. In addition, minerals such as zinc (Zn), iron (Fe), calcium (Ca), chromium (Cr), magnesium (Mg), manganese (Mn), and copper (Cu) may be included. In addition, amino acids such as lysine, tryptophan, cysteine, and valine may be included. In addition, the food composition may be added with food additives, such as preservatives (potassium sorbate, sodium benzoate, salicylic acid, sodium dehydroacetate, etc.), disinfectants (bleaching powder and highly bleaching powder, sodium hypochlorite, etc.), antioxidants (butylhydroxyanisole (BHA), butylhydroxytoleuene (BHT), etc.), colorants (tar color, etc.), coloring agents (sodium nitrite, etc.), bleach (sodium sulfite), seasoning (MSG sodium glutamate, etc.), sweeteners (dulcin, cyclamate, saccharin, sodium, etc.), flavorings (vanillin, lactones, etc.), expanding agents (alum, potassium D-bitartrate, etc.), reinforcing agents, emulsifying agents, thickening agents, coating agents, gum base agents, foam inhibitors, solvents, improving agents, etc. The additive is selected according to a type of food and used in an appropriate amount.

The food composition may be specifically a health functional food composition.

As a specific example, processed foods capable of promoting height growth may be produced using the food composition, and for example, the food composition may be produced as health functional foods in the forms of confectionery, beverages, alcoholic drinks, fermented foods, canned foods, processed milk foods, processed meat foods, or processed noodles. At this time, the confectionery includes biscuits, pies, cakes, bread, candy, jelly, gum, cereals (including meal substitutes such as grain flakes), and the like. The beverages include drinking water, carbonated beverages, functional ionic beverages, juices (for example, apple, pear, grape, aloe, tangerine, peach, carrot, tomato juices, etc.), sikhye, and the like. The alcoholic drinks include sake, whiskey, shochu, beer, hard liquor, and fruit liquor. The fermented foods include soy sauce, soybean paste, and red pepper paste. The canned foods include canned seafood (for example, canned tuna, mackerel, saury, conch, etc.), canned livestock (canned beef, pork, chicken, turkey, etc.), and canned agricultural products (canned corn, peaches, pile apple, etc.). The milk processed foods include cheese, butter, and yogurt. The processed meat foods include pork cutlet, beef cutlet, chicken cutlet, sausage, sweet and sour pork, nuggets, neobiani, etc. The processed noodles include dried noodles, thin noodles, ramen, udon noodles, cold noodles, sealed packaged fresh noodles, etc. In addition, the composition may be used for retort foods, soups, and the like.

The term "health functional food" of the present invention, as the same term as food for special health use (FoSHU), refers to foods with high medical and health effects that have been processed to efficiently show a body modulating function in addition to supplying nutrients. The foods may be produced in various forms such as tablets, capsules, powders, granules, liquids, pills, etc., in order to obtain a useful effect in promoting height growth.

The composition for promoting height growth of the present invention may comprise the *Humulus japonicus* ingredient in an amount of 0.1 to 100 wt %, more preferably 20 to 99 wt %, based on the total weight of the composition.

The composition for promoting height growth of the present invention may comprise the *Humulus japonicus* ingredient and at least one selected from the group consisting of watermelon and garlic in an amount of 0.1 to 100 wt %, more preferably 20 to 99 wt %, based on the total weight of the composition.

The composition for promoting height growth of the present invention may be administered in an amount of 1 mg to 30 g once based on the used amount of *Humulus japonicus*, and may be administered 2 to 3 times a day. Specifically, in the case of the extract, the extract prepared by using the *Humulus japonicus* in the content range may be considered as a single and daily dose. However, the present invention is not limited thereto, and may be determined by comprehensively considering various situations as described above.

The composition for promoting height growth of the present invention provides an effect of activating the proliferation of MG63 cells. In addition, the composition for promoting height growth increases ALP and osteocalcin (OC) gene expression in MG63 cells, and provides an effect of increasing the concentration of IGF-1 protein.

The ALP and osteocalcin are genes related to bone formation and are known to increase activities thereof when bone growth occurs actively, and the osteocalcin is a protein synthesized by osteoblasts during bone remodeling and bound to the extracelluar matrix of the bone.

The IGF-1 protein is an ingredient produced and secreted by growth hormones.

Modes of the Invention

Hereinafter, the present invention will be described in more detail with reference to Examples. However, the following Examples are for explaining the present invention in more detail, and the scope of the present invention is not limited by the following Examples. The following Examples can be appropriately modified and changed by those skilled in the art within the scope of the present invention.

Example 1: Preparation of Hot Water Extract of *Humulus japonicus*

100 g of leaves and sprouts of *Humulus japonicus* were added with 2 L of distilled water and extracted with hot water at 90° C. for 5 hours. The extract was filtered, and the filtered extract solution was concentrated under reduced pressure at 50° C. to obtain a powdered sample through freeze-drying. At this time, the yield was 16.3 wt %.

Example 2: Preparation of Ethanol Extract of *Humulus japonicus*

100 g of leaves and sprouts of *Humulus japonicus* were added with 2 L of 50% ethanol and extracted at 50° C. for 5 hours. The extract was filtered, and the filtered extract solution was concentrated under reduced pressure at 40° C. to obtain a powdered sample through freeze-drying. At this time, the yield was 15.2 wt %.

Example 3: Preparation of Acetone Extract of *Humulus japonicus*

100 g of leaves and sprouts of *Humulus japonicus* were added with 2 L of 99% acetone and extracted at 50° C. for 5 hours. The extract was filtered, and the filtered extract solution was concentrated under reduced pressure at 40° C. to obtain a powdered sample through freeze-drying. At this time, the yield was 3.7 wt %.

Example 4: Preparation of Ethyl Acetate Extract of *Humulus Japonicus*

100 g of leaves and sprouts of *Humulus japonicus* were added with 2 L of 99% ethyl acetate and extracted at 0° C. for 5 hours. The extract was filtered, and the filtered extract solution was concentrated under reduced pressure at 40° C. to obtain a powdered sample through freeze-drying. At this time, the yield was 4.2 wt %.

Example 5: Preparation of Watermelon/Garlic Concentrate 16 kg of peeled garlic and 8 kg of seed-removed watermelon juice were heated in a high-pressure gas cooker under a pressure of 1 to 1.5 kg for 16 hours, and then dried and powdered.

Examples 6 to 8: Preparation of Compositions Containing *Humulus japonicus* Extract and Watermelon/Garlic Concentrate The hot water extract powder of *Humulus japonicus* prepared in Example 1 and the watermelon/garlic concentrate powder prepared in Example 5 were mixed in a composition ratio of Table below to prepare a composition containing the *Humulus japonicus* extract and the watermelon/garlic concentrate.

TABLE 1

| | Hot water extract powder of Humulus japonicus of Example 1 | Watermelon/garlic concentrate powder of Example 5 |
|---|---|---|
| Composition of Example 6 | 20 wt % | 80 wt % |
| Composition of Example 7 | 50 wt % | 50 wt % |
| Composition of Example 8 | 80 wt % | 20 wt % |

Experimental Example 1: Evaluation of Cytotoxicity

In Experimental Example 1, the following experiment was performed to confirm effects of *Humulus japonicus* extracts in Examples 1 to 4 of the present invention and a watermelon/garlic concentrate sample in Example 5 on cytotoxicity.

$1 \times 10^4$ MG63 cells were dispensed into a 96 well plate, and a DMEM containing 10% FBS was used as a culture medium. After incubation for 12 hours, each extract and the watermelon/garlic concentrate were treated with 100 to 1000 μg/mL and incubated for 24 hours. Thereafter, 20 μL of a WST reagent was added to block light with a foil to minimize WST reduction by light and reacted for 3 hours. The optical density was measured at a wavelength of 560 nm using an iMARK™ Microplate reader (Bio-Rad Laboratories Headquarters, Hercules, Calif., USA), and the results were shown in Table 2 below.

As shown in Table 2 below, as a result of evaluating the cytotoxicity of each sample by $ED_{50}$ (a concentration at which cell viability becomes 50%), an ethyl acetate extract showed toxicity at the lowest concentration of 350.6 μg/mL.

Therefore, it was shown that all test ingredients were safe at concentrations below 350 μg/mL.

TABLE 2

| Samples | $ED_{50}$ (μg/mL) |
|---|---|
| Example 1: Hot water extract of Humulus japonicus | 1397.8 |
| Example 2: Ethanol extract of Humulus japonicus | 760.4 |
| Example 3: Acetone extract of Humulus japonicus | 410.2 |
| Example 4: Ethyl acetate extract of Humulus japonicus | 350.6 |
| Example 5: Watermelon/garlic concentrate powder | 860.6 |

Experimental Example 2: Evaluation of Proliferation of MG63 Cells

The following experiment was performed to confirm effects of the *Humulus japonicus* extracts in Examples 1 to 4 of the present invention and the watermelon/garlic concentrate sample in Example 5 on proliferation of MG63 cells.

$1 \times 10^4$ MG63 cells were dispensed into a 96 well plate, and a DMEM containing 10% FBS was used as a culture medium. After incubation for 12 hours, each *Humulus japonicus* extract and the watermelon/garlic concentrate were treated with 100 μg/mL and incubated for 24 hours. Thereafter, 20 μL of a WST reagent was added to block light with a foil to minimize WST reduction by light and reacted for 3 hours. The optical density was measured at a wavelength of 560 nm using an iMARK™ Microplate reader (Bio-Rad Laboratories Headquarters, Hercules, Calif., USA).

The results of evaluating cell proliferation of respective samples were shown in FIG. 1. As shown in FIG. 1, the hot water extract of *Humulus japonicus* showed an increase in cell activity of 146.95% compared to a normal group, and the ethanol extract showed an increase in activity of 131.75%. In addition, compared to the normal group, the acetone and ethyl acetate extracts showed increases in activity of 113.70% and 105.41%, respectively. In the group treated with the watermelon/garlic concentrate, a significant increase in activity was confirmed with respect to the normal group by 133.30%.

Experimental Example 3: Measurement of Expression of ALP and Osteocalcin (OC) Genes and Concentration of IGF-1 Protein in MG63 Cells The following experiment was performed to confirm effects of the *Humulus japonicus* extracts in Examples 1 to 4 of the present invention and the watermelon/garlic concentrate sample in Example 5 on the expression of ALP and OC genes and the concentration of IGF-1 protein in MG63 cells.

$5 \times 10^5$ MG63 cells were dispensed into a 12 well plate, treated with 100 μg/Ml of the *Humulus japonicus* extracts and the watermelon/garlic concentrate for 24 hours, and then the cells were collected and RNA extraction was performed according to a manufacturer's protocol by using an RNeasy extraction kit (Qiagen, Gaithersburg, Md., USA). cDNA was synthesized by using an iScript cDNA synthesis kit (Bio-Rad Laboratories Headquarters, Hercules, Calif., USA). Real-time quantitative PCR was performed using SYBR Green (iQ SYBR Green Supermix, Bio-Rad Laboratories Inc.) to measure the expression of genes, and as an instrument, Real-Time PCR (Applied Biosystems, Foster City, Calif., USA) was used. The nucleotide sequences of the genes to be measured were shown in Table 3 below.

For real time PCR reaction, 2 μL of cDNA and 10 μL of 2×SYBR mix were added in a total of 20 μL, and 100 pmol/μL of forward and reverse primers were added by 1 μL, respectively, and the remaining primers were filled with $H_2O$. Amplification was performed through a PCR amplification step as follows, and 40 cycles of amplification cycle were performed. In other words, hot start at 95° C. for 8 minutes, denaturation in the amplification step at 95° C. for 15 seconds, annealing at 55° C. for 30 seconds, and extension at 72° C. for 30 seconds were repeated, and the values were recorded after the extension of each cycle. After all cycles were completed, melting curve analysis was performed to confirm the specificity of the primers. The results were analyzed with One step system software v2.1 provided by Applied Biosystems. The concentration of IGF-1 protein was measured using an enzyme assay kit (Crystal Chem, IL, USA) according to a manufacturer's protocol.

As a result of measuring ALP gene expression, as shown in FIG. 2, groups treated with the samples prepared in Examples 1 to 5 increased in the expression level of the ALP gene compared to a group not treated with the samples. In other words, the groups treated with the ethanol extract, the hot water extract, and the watermelon/garlic concentrate showed a significant increase compared to the group not treated with the samples, and in particular, the hot water extract increased the expression level of the ALP gene by 471.05% compared to the sample normal group.

As a result of measuring OC gene expression, as shown in FIG. 3, the groups treated with the samples prepared in Examples 1 to 5 increased in the expression level of the OC gene compared to a group not treated with the samples. In particular, the group treated with the hot water extract showed a significant difference as the expression of the OC gene increased by 346.10% compared to the normal group.

As a result of measuring the concentration of the IGF-1 protein, as shown in FIG. 4, the groups treated with the samples prepared in Examples 1 to 5 increased the concentration of the IGF-1 protein compared to the group not treated with the samples. In particular, the group treated with the hot water extract showed a significant increase in protein expression level of IGF-1 by 248.31% compared to the normal group.

TABLE 3

| Gene | Primer sequences |
|---|---|
| GAPDH | F 5'-CCCCACACACATGCACTTACC-3'<br>R 5'-TTGCCAAGTTGCCTGTCCTT-3' |

TABLE 3-continued

| Gene | Primer sequences |
|---|---|
| ALP | F 5'-CCGCTTTAACCAGTGCAACA-3' |
|  | R 5'-CCCGATTCATCACGGAGATG-3' |
| Osteocalcin | F 5'-CAGGAGGGCAGCGAGGTA-3' |
|  | R 5'-GCTCCCAGCCATTGATACA-3' |

Experimental Example 4: Evaluation of Proliferation of MG63 Cells According to Mixing Ratio of Composition of Hot Water Extract of *Humulus japonicus* and Watermelon/Garlic Concentration In order to confirm effects of treatment of the compositions containing the *Humulus japonicus* extract and the watermelon/garlic concentrate in Examples 6 to 8 of the present invention prepared by varying a mixing ratio on proliferation of MG63 cells, respectively, the following experiment was performed.

$1 \times 10^4$ MG63 cells were dispensed into a 96 well plate, and a DMEM containing 10% FBS was used as a culture medium. After incubation for 12 hours, the compositions containing the hot water extract of *Humulus japonicus* and the watermelon/garlic concentrate [weight ratio of *Humulus japonicus* extract and watermelon/garlic concentrate=2:8 (Example 6), 5:5 (Example 7), 8:2 (Example 8)] were treated with 10, 50, and 100 μg/mL, respectively, and incubated for 24 hours. The following experimental method was performed in the same manner as in Experimental Example 3.

As a result of performing the experiment, as shown in FIG. 5, test groups treated with the compositions of the *Humulus japonicus* extract and the watermelon/garlic concentrate in Examples 6 to 8 showed increases in cellular activity compared to the normal group. In addition, in the test groups treated with the compositions (Examples 6 to 8) containing the *Humulus japonicus* extract and the watermelon/garlic concentrate, more effective cell activity was observed than in the test groups (Examples 1 to 5) treated with the *Humulus japonicus* extracts and the watermelon/garlic concentrate as a single ingredient. Regarding the mixing ratio, it was confirmed that as the content of the *Humulus japonicus* extract was higher and the concentration of the composition was higher, the cell activity was increased.

Experimental Example 5: Measurement of Expression of ALP and Osteocalcin (OC) Genes and Concentration of IGF-1 According to Mixing Ratio of Composition of Hot Water Extract of *Humulus japonicus* and Watermelon/Garlic Concentrate In order to confirm effects of treatment of the compositions containing the *Humulus japonicus* extract and the watermelon/garlic concentrate in Examples 6 to 8 of the present invention prepared by varying a mixing ratio on ALP, OC, and IGF-1 genes in MG63 cells, respectively, the following experiment was performed.

$5 \times 10^5$ MG63 cells were dispensed into a 12 well plate, and the compositions containing the hot water extract of *Humulus japonicus* and the watermelon/garlic concentrate [weight ratio of *Humulus japonicus* extract and watermelon/garlic concentrate=2:8 (Example 6), 5:5 (Example 7), 8:2 (Example 8)] were treated with 10, 50, and 100 μg/mL for 24 hours, respectively. Then, the cells were collected and RNA extraction was performed by a RNeasy extraction kit (Qiagen, Gaithersburg, Md., USA) according to a manufacturer's protocol. The following experimental method was the same as in Experimental Example 4.

As a result of measuring ALP gene expression, as shown in FIG. 6, all groups treated with the extracts increased in the expression level of the ALP gene compared to a group not treated with the extracts. In the single-treated group, the expression level of ALP in the hot water extract treated group (Example 1) of *Humulus japonicus* was increased more than that of the watermelon/garlic treated group (Example 5), and in the groups treated with the compositions containing the hot water extract of *Humulus japonicus* and the watermelon/garlic concentrate in Examples 6 to 8, the expression level of ALP was more increased than that of a single treated group of the hot water extract of *Humulus japonicus* in Example 1. Among the composition treated groups, it was confirmed that as the content of the hot water extract of *Humulus japonicus* was higher and the treated concentration of the sample was higher, the expression level of ALP was more increased.

As a result of measuring the expression of the OC gene, as shown in FIG. 7, the gene expression levels were increased in all sample treated groups, and in the single-treated group, the expression of the OC gene in the hot water extract treated group (Example 1) of *Humulus japonicus* was increased more than that of the watermelon/garlic treated group (Example 5).

In addition, in the groups treated with the compositions containing the hot water extract of *Humulus japonicus* and the watermelon/garlic concentrate in Examples 6 to 8, the expression level of the OC gene was more increased than that of the single treated group of the hot water extract of *Humulus japonicus* in Example 1. Particularly, among the composition treated groups, it was confirmed that as the content of the hot water extract of *Humulus japonicus* was higher and the treated concentration of the sample was higher, the expression level of the OC gene was more increased.

As a result of measuring the concentration of the IGF-1 protein, as shown in FIG. 8, the concentrations of the IGF-1 protein were increased in all sample treated groups, and in the single treated group, the concentration of the IGF-1 protein in the hot water extract treated group (Example 1) of *Humulus japonicus* was shown higher than that of the watermelon/garlic treated group (Example 5).

In addition, in the groups treated with the compositions containing the hot water extract of *Humulus japonicus* and the watermelon/garlic concentrate in Examples 6 to 8, the concentration of the IGF-1 protein was higher than that of the single treated group of the hot water extract of *Humulus japonicus* in Example 1. Particularly, among the composition treated groups, it was confirmed that as the content of the hot water extract of *Humulus japonicus* was higher and the treated concentration of the sample was higher, the concentration of the IGF-1 protein was higher.

Experimental Example 6: Growth Promotion Experiment of SD Rat

In Experimental Example 6, the following experiment was performed in order to confirm an effect on the height growth of SD rats when the hot water extract of *Humulus japonicus* of the present invention and the watermelon/garlic concentrate were treated by varying a mixing ratio.

3-week-old SD rats were supplied by Saeron Bio Co., Ltd. and adapted to a surrounding environment for 1 week under certain conditions (temperature: 23±2° C., relative humidity: 50±5%, contrast: 12 hours light/dark cycle) in an animal breeding room and then used. For animals determined to be healthy during the adaptation period, subjects close to an average weight were selected, and groups were divided using 6 rats per group using a random method.

The groups were divided into a normal control (NC), a control (recombinant growth hormone; growth hormone administered group), 50 mg/kg B.W. of the hot water extract of *Humulus japonicus* of Example 1; 100 mg/kg B.W. of the hot water extract of *Humulus japonicus* of Example 1; 50 mg/kg B.W. of the watermelon/garlic concentrate of Example 5; 100 mg/kg B.W. of the watermelon/garlic concentrate of Example 5; 50 mg/kg B.W. of the composition containing the hot water extract of *Humulus japonicus* and the watermelon/garlic concentrate of Example 6 (weight ratio=20:80); 100 mg/kg B.W. of the composition containing the hot water extract of *Humulus japonicus* and the watermelon/garlic concentrate of Example 6 (weight ratio=20:80); 50 mg/kg B.W. of the composition containing the hot water extract of *Humulus japonicus* and the watermelon/garlic concentrate of Example 7 (weight ratio=50:50); 100 mg/kg B.W. of the composition containing the hot water extract of *Humulus japonicus* and the watermelon/garlic concentrate of Example 7 (weight ratio=50:50); 50 mg/kg B.W. of the composition containing the hot water extract of *Humulus japonicus* and the watermelon/garlic concentrate of Example 8 (weight ratio=80:20); and 100 mg/kg B.W. of the composition containing the hot water extract of *Humulus japonicus* and the watermelon/garlic concentrate of Example 8 (weight ratio=80:20). AIN93G diet and drinking water were supplied freely for 3 weeks. During the experimental period, the body weights and animal lengths (nose-anus length and nose-tail length) were measured every week at a certain time, and the results were shown in Table 4 below.

TABLE 4

| Test group | Ingredients | Dose | Body weight gain (g) | Nose-anus length gain (%) | Nose-tail length gain (%) |
|---|---|---|---|---|---|
| NC | No control | — | 95.97 ± 3.71$^c$ | 22.98 ± 1.00$^i$ | 21.27 ± 1.35$^i$ |
| C | Growth hormone | 0.1 IU/kg | 118.14 ± 4.99$^a$ | 37.54 ± 0.35$^a$ | 37.34 ± 0.17$^a$ |
| Example 1 | Hot water extract of *Humulus japonicus* | 50 mg/kg B.W. | 113.59 ± 3.02$^{ab}$ | 33.47 ± 0.20$^f$ | 33.40 ± 0.15$^f$ |
| | | 100 mg/kg B.W. | 109.98 ± 1.51$^b$ | 34.62 ± 0.60$^{de}$ | 34.36 ± 0.19$^{de}$ |
| Example 5 | Watermelon/garlic concentrate | 50 mg/kg B.W. | 107.51 ± 5.51$^b$ | 26.05 ± 0.84$^h$ | 25.88 ± 0.42$^h$ |
| | | 100 mg/kg B.W. | 108.03 ± 5.86$^b$ | 28.01 ± 0.63$^g$ | 27.72 ± 0.38$^g$ |
| Example 6 | *Humulus japonicus*: Watermelon/garlic concentrate 20:80 (wt %) | 50 mg/kg B.W. | 112.54 ± 4.87$^{ab}$ | 34.25 ± 0.67$^{ef}$ | 33.58 ± 0.53$^{ef}$ |
| | | 100 mg/kg B.W. | 110.15 ± 4.96$^b$ | 33.93 ± 0.65$^{ef}$ | 33.66 ± 0.77$^{ef}$ |
| Example 7 | *Humulus japonicus*: Watermelon/garlic concentrate 50:50 (wt %) | 50 mg/kg B.W. | 110.59 ± 5.37$^b$ | 34.01 ± 0.63$^{ef}$ | 33.73 ± 0.28$^{ef}$ |
| | | 100 mg/kg B.W. | 106.42 ± 4.89$^b$ | 35.32 ± 0.46$^{cd}$ | 34.59 ± 0.46$^d$ |
| Example 8 | *Humulus japonicus*: Watermelon/garlic concentrate 80:20 (wt %) | 50 mg/kg B.W. | 112.24 ± 4.47$^{ab}$ | 36.11 ± 0.24$^{bc}$ | 35.46 ± 0.41$^c$ |
| | | 100 mg/kg B.W. | 112.30 ± 2.86$^{ab}$ | 36.48 ± 0.73$^b$ | 36.32 ± 0.53$^b$ |

As shown in Table 4, as a result of measuring the body lengths of the experimental animals after oral administration of each sample, it was confirmed that in a control group administered with a growth hormone, compared to a normal group without administration of the sample, a length from nose to hip was significantly increased by 22.98 to 37.54%, and a length from nose to tail was also significantly increased by 21.27 to 37.34%. In the sample administered group in Example of the present invention, compared to the normal group, the length from the nose to the hip was significantly increased by 26.05 to 36.48% and the length from the nose to the tail was also significantly increased by 25.88 to 36.32%.

Specifically, as in the cell experiment, when the hot water extract of *Humulus japonicus* of Example 1 was administered alone, compared to the case where the watermelon/garlic concentrate of Example 5 was administered alone, a better length increase was shown.

In addition, in the groups treated with the compositions containing the hot water extract of *Humulus japonicus* and the watermelon/garlic concentrate in Examples 6 to 8, the increase in lengths of the experimental animals was greater than that of a single treated group of the hot water extract of *Humulus japonicus*.

Particularly, among the composition treated groups, it was confirmed that as the content of the hot water extract of *Humulus japonicus* was higher and the treated concentration of the sample was higher, the increase in lengths of the experimental animals was greater.

The invention claimed is:

1. A method for promoting height growth of a subject in need thereof, comprising administering to the subject an effective amount of a food composition comprising a water extract of *Humulus japonicus* plant material as an active ingredient, wherein the subject is a child and/or an adolescent.

2. The method of claim 1, wherein the *Humulus japonicus* plant material is selected at one selected from the group consisting of: leaves, sprouts, stems, and roots.

3. The method of claim 1, wherein the food composition further comprises
at least one selected from the group consisting of watermelon and garlic.

4. The method of claim 3, wherein the at least one selected from the group consisting of watermelon and garlic is in a form of a concentrate.

* * * * *